US010758676B2

(12) United States Patent
Baker et al.

(10) Patent No.: US 10,758,676 B2
(45) Date of Patent: Sep. 1, 2020

(54) DRUG DELIVERY DEVICE WITH ELECTRO-MECHANIC DRIVE MECHANISM

(71) Applicant: SANOFI-AVENTIS DEUTSCHLAND GMBH, Frankfurt am Main (DE)

(72) Inventors: Alex John Baker, Warwickshire (GB); James Andrew Holt, Warwickshire (GB); Timothy Lewis Sharpe, Warwickshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 99 days.

(21) Appl. No.: 15/226,592

(22) Filed: Aug. 2, 2016

(65) Prior Publication Data

US 2016/0339178 A1 Nov. 24, 2016

Related U.S. Application Data

(63) Continuation of application No. 14/130,034, filed as application No. PCT/EP2012/063633 on Jul. 12, 2012, now Pat. No. 9,440,028.

(Continued)

(30) Foreign Application Priority Data

Jul. 15, 2011 (EP) .................................... 11174125

(51) Int. Cl.
*A61M 5/20* (2006.01)
*A61M 5/315* (2006.01)
*A61M 5/24* (2006.01)

(52) U.S. Cl.
CPC ................ *A61M 5/20* (2013.01); *A61M 5/24* (2013.01); *A61M 5/31546* (2013.01);
(Continued)

(58) Field of Classification Search
CPC .... A61M 2005/31588; A61M 5/31525; A61M 5/31548
(Continued)

(56) References Cited

U.S. PATENT DOCUMENTS

| 533,575 A | 2/1895 | Wilkens |
| 4,943,279 A | 7/1990 | Samiotes et al. |

(Continued)

FOREIGN PATENT DOCUMENTS

| CN | 1042659 | 6/1990 |
| CN | 1494927 | 5/2004 |

(Continued)

OTHER PUBLICATIONS

International Search Report for Int. App. No. PCT/EP2012/063633, completed Aug. 16, 2012.
(Continued)

*Primary Examiner* — Deanna K Hall
(74) *Attorney, Agent, or Firm* — Fish & Richardson P.C.

(57) ABSTRACT

The present invention relates to a drug delivery device for setting and dispensing of a dose of a medicament is presented comprising a housing to accommodate a cartridge filled with the medicament, an electrically operated drive mechanism to be operably engaged with the cartridge to expel a predefined dose of the medicament from the cartridge, and at least one dose element displaceably arranged relative to the housing to set and/or to dispense the dose of the medicament, wherein the dose element and the drive mechanism are mechanically decoupled from each other.

24 Claims, 2 Drawing Sheets

Related U.S. Application Data

(60) Provisional application No. 61/570,307, filed on Dec. 14, 2011.

(52) U.S. Cl.
CPC .... *A61M 5/31551* (2013.01); *A61M 5/31553* (2013.01); *A61M 5/31555* (2013.01); *A61M 5/31578* (2013.01); *A61M 5/31583* (2013.01); *A61M 2005/31588* (2013.01); *A61M 2205/332* (2013.01)

(58) Field of Classification Search
USPC .......................................................... 604/207
See application file for complete search history.

(56) References Cited

U.S. PATENT DOCUMENTS

| | | | |
|---|---|---|---|
| 4,950,246 | A | 8/1990 | Muller |
| 5,226,895 | A | 7/1993 | Harris |
| 5,279,586 | A | 1/1994 | Balkwill |
| 5,304,152 | A | 4/1994 | Sams |
| 5,320,609 | A | 6/1994 | Haber et al. |
| 5,383,865 | A | 1/1995 | Michel |
| 5,480,387 | A | 1/1996 | Gabriel et al. |
| 5,505,704 | A | 4/1996 | Pawelka et al. |
| 5,536,249 | A | 7/1996 | Castellano et al. |
| 5,582,598 | A | 12/1996 | Chanoch |
| 5,626,566 | A | 5/1997 | Petersen et al. |
| 5,674,204 | A | 10/1997 | Chanoch |
| 5,688,251 | A | 11/1997 | Chanoch |
| 5,921,966 | A | 7/1999 | Bendek et al. |
| 5,961,495 | A | 10/1999 | Walters et al. |
| 6,004,297 | A | 12/1999 | Steenfeldt-Jensen et al. |
| 6,193,698 | B1 | 2/2001 | Kirchhofer et al. |
| 6,221,046 | B1 | 4/2001 | Burroughs et al. |
| 6,235,004 | B1 | 5/2001 | Steenfeldt-Jensen et al. |
| 6,248,095 | B1 | 6/2001 | Giambattista et al. |
| 6,482,185 | B1 | 11/2002 | Hartmann |
| 6,585,698 | B1 * | 7/2003 | Packman ................. A61M 5/24 604/207 |
| 6,899,698 | B2 | 5/2005 | Sams |
| 6,936,032 | B1 | 8/2005 | Bush, Jr. et al. |
| 7,241,278 | B2 | 7/2007 | Moller |
| 8,043,254 | B2 * | 10/2011 | Chavez ................... A61M 5/20 604/67 |
| 8,708,957 | B2 * | 4/2014 | Jespersen ............ A61M 5/1452 604/135 |
| 2002/0052578 | A1 | 5/2002 | Moller |
| 2002/0107477 | A1 | 8/2002 | Kipfer |
| 2002/0120235 | A1 | 8/2002 | Enggaard |
| 2003/0040716 | A1 | 2/2003 | Heiniger et al. |
| 2003/0050609 | A1 | 3/2003 | Sams |
| 2004/0059299 | A1 | 3/2004 | Moller |
| 2004/0210199 | A1 | 10/2004 | Atterbury et al. |
| 2004/0267207 | A1 | 12/2004 | Veasey et al. |
| 2005/0113765 | A1 | 5/2005 | Veasey et al. |
| 2006/0153693 | A1 | 7/2006 | Fiechter et al. |
| 2008/0287865 | A1 | 11/2008 | Nielsen et al. |
| 2008/0312604 | A1 | 12/2008 | Boesen |
| 2009/0275916 | A1 | 11/2009 | Harms et al. |

FOREIGN PATENT DOCUMENTS

| | | |
|---|---|---|
| CN | 101198366 | 6/2008 |
| EP | 0293958 | 12/1988 |
| EP | 0937471 | 8/1999 |
| EP | 0937476 | 8/1999 |
| EP | 1074273 | 2/2001 |
| WO | WO 1997/014459 | 4/1997 |
| WO | 99/38554 | 8/1999 |
| WO | 01/10484 | 2/2001 |
| WO | 2005/004955 | 1/2005 |
| WO | WO 2006/134153 | 12/2006 |
| WO | 2007/099093 | 9/2007 |

OTHER PUBLICATIONS

International Preliminary Report on Patentability in Application No. PCT/EP2012/063633, dated Jan. 21, 2014, 5 pages.

* cited by examiner

DRUG DELIVERY DEVICE WITH ELECTRO-MECHANIC DRIVE MECHANISM

CROSS REFERENCE TO RELATED APPLICATIONS

The present application is a continuation of U.S. patent application Ser. No. 14/130,034, filed Dec. 30, 2013, which is a U.S. National Phase Application pursuant to 35 U.S.C. § 371 of International Application No. PCT/EP2012/063633 filed Jul. 12, 2012, which claims priority to European Patent Application No. 11174125.2 filed Jul. 15, 2011, and U.S. Provisional Patent Application No. 61/570,307, filed Dec. 14, 2011. The entire disclosure contents of these applications are herewith incorporated by reference into the present application.

TECHNICAL FIELD

The present invention relates to a drug delivery device having an electro-mechanical drive mechanism to dispense a predefined dose of a medicament from a cartridge. The electro-mechanical drug delivery device is particularly adapted to imitate or to mimic mechanical properties of an all-mechanical or manually operated drug delivery device.

BACKGROUND

User operated drug delivery devices are as such known in the art. They are typically applicable in circumstances, in which persons without formal medical training, i.e., patients, need to administer an accurate and predefined dose of a medicament, such as heparin or insulin. In particular, such devices have application, where a medicament is administered on a regular or irregular basis over a short-term or long-term period.

In order to accommodate with these demands, such devices have to fulfil a number of requirements. First of all, the device must be robust in construction, yet easy to use in terms of handling and in understanding by the user of its operation and the delivery of the required dose or medicament. The dose setting must be easy and unambiguous. Where the device is to be disposable rather than reusable, the device should be inexpensive to manufacture and easy to dispose.

Apart from manually or purely mechanically operated drug delivery devices there also exist electro-mechanical drug delivery devices wherein dose selection and administration of an appropriate dose of the medicament is controlled by way of electronic circuitry, for example a controller, a microprocessor, and/or the like. Such electronic or electro-mechanical devices provide a high dosing accuracy and may support long-term monitoring of doses dispensed by the device. Hence, a dosing and dispensing scheme can even be stored in the device allowing to recall the dose dispensing history.

However, with electronic or electro-mechanical devices, setting and dispending of a dose might be less intuitive compared to an all-mechanically implemented device. In particular, with a mechanically implemented device, the user has to apply a certain injection force, thereby obtaining a force feedback. By introducing an electro-mechanical device and replacing an all-mechanical device, the patient or user may be confronted with an unfamiliar or inconvenient operation scheme. Hence, there may emerge a certain danger of misuse and suboptimal medical treatment. Also, the acceptance of such an electro-mechanical device by the user may be rather low.

It is therefore an object of the present invention to provide an electro-mechanical drug delivery device providing a higher level of user acceptance, especially with users that are accustomed to mechanically implemented devices. Hence, the invention aims to enhance user compliance for electro-mechanically implemented devices. With the invention, users that are used to the functionality of a mechanical drug delivery device should become accustomed to an electrically driven device more easily.

SUMMARY

The drug delivery device according to the present invention is adapted and intended for setting and dispensing of a dose of a medicament. The drug delivery device comprises a housing to accommodate a cartridge being at least partially filled with the medicament to be dispensed. The device further comprises an electrically operated drive mechanism to become operably engaged with the cartridge to expel a predefined dose of the medicament from the same. Preferably, the cartridge comprises a piston slidably disposed therein that serves as a proximal seal of the cartridge's body. The drive mechanism, typically comprising a piston rod is then adapted to exert distally directed pressure to the piston in order to increase the fluid pressure inside the cartridge and to expel the required dose of the medicament via a distally located septum to be penetrated by a piercing element, such as an injection needle or the like.

Moreover, the drug delivery device also comprises at least one dose element being displaceably arranged relative to the housing to set and/or to dispense the dose of the medicament. According to one embodiment, the movability of the dose element relative to the housing could serve to mimic and/or to imitate the operability or functionality of an all-mechanical drug delivery device. Even though the at least one dose element may serve as an actuator, it is in fact mechanically decoupled from the electrically implemented drive mechanism. In this way, an electrically implemented or electro-mechanical drug delivery can be provided wherein a dose element is displaceably, hence, rotationally and/or translationally supported with respect to the housing.

Rotational and/or translational or longitudinal displacement of the dose element relative to the housing is conducted for the purpose to imitate and/or to mimic operability of a mechanically implemented or manually driven drug delivery device. In general, the dose element may serve as a component to enhance patient and user compliance.

Dose setting is conducted by rotational and/or translational or longitudinal displacement of the dose element. The dose element is mechanically separated from the electrically implemented drive mechanism. There is no mechanical coupling or linkage configured to transfer displacement of the dose element to the drive mechanism.

Dose dispensing is in fact entirely conducted by an electro-mechanical implementation of the drive mechanism. Hence, the dose dispensing or medicament injection procedure may only be triggered by a user. The process of expelling the medicament from the cartridge is implemented electro-mechanically and may follow a predefined schedule. Respective forces to be applied, e.g. to a cartridge will be provided by an electrical drive.

According to a preferred embodiment, the dose element is translationally and/or rotatably mounted relative to the housing. In case the drug delivery device is implemented as a pen-type injector of elongated geometry, the dose element may be located near a proximal end of the device facing away from a treatment area of the patient. In the course of a dose setting procedure, the dose element may be translationally and/or rotatably displaced in proximal direction relative to the housing, thereby protruding and separating from the proximal end of the housing.

According to another preferred aspect, the position and/or orientation of the dose element relative to the housing is indicative of the size of the dose to be injected by the device. Preferably, the dose element is provided with a scale, which according to a specific position or orientation of the dose element, is indicative of the number of units of the medicament that will be dispensed in a subsequent dispensing or injection procedure.

In another preferred aspect, the dose element is also operable to initiate and/or to control a dose dispensing operation of the drive mechanism. However, since the drive mechanism is electrically driven, actuation of the dose element is monitored by means of at least one sensor element. The electrical signal attainable from said sensor is provided to the drive mechanism, where the sensor signal can be appropriately processed in order to effectuate a respective dispensing procedure.

Correspondingly, and according to another preferred embodiment, the device comprises at least one position sensor and/or at least one rotation sensor to detect the position and/or the orientation of the dose element relative to the housing. Said position and/or rotation sensor may be further adapted to monitor and to quantify the velocity of a movement of the dose element. By determining or detecting the position and/or orientation of the dose element, the drive mechanism may determine or calculate the size of the dose to be injected in a subsequent dose dispensing procedure.

Positioning and/or rotation sensors may be implemented optically, magnetically and/or electrically, so that the position or angle is encoded relatively, for example relatively to an earlier position, or absolutely, for example with respect to the housing. The sensor element(s) may comprise hall-elements or comparable magneto-resistive components whereas the dose element is magnetically encoded according to its degree of freedom.

In another preferred embodiment, the drug delivery device further comprises at least one force or pressure sensor to determine a force acting on the dose element during dose injection. In this way, distally directed forces provided and supplied by a user can be detected and optionally recorded, and the dose dispensing procedure may be conducted accordingly. Hence, the magnitude of the applied force or pressure may govern the velocity of the electro-mechanically implemented dose dispensing. For example, if the applied force is above a threshold, the medicament is delivered at a predefined rate, for example 8 units/second.

According to a further preferred embodiment, the drug delivery device also comprises at least one actuator to displace and/or to rotate the dose element to an initial position or initial orientation during an electrically operated dose dispensing action of the drive mechanism. Hence, the actuator may provide mechanical feedback to the user regarding the electrically implemented dose dispensing action. The actuator may be further controlled by the electrically implemented drive mechanism in such a way, that a momentary position or movement of the dose element reflects the actual dose dispensing procedure conducted by the drive mechanism.

The actuator, typically comprising an electric drive generates and provides a counter force to the user in order to mimic or to imitate at least one or more aspects of the operability of an all-mechanically implemented drug delivery device. Preferably, the displacement and/or rotation of the dose element towards an initial position or configuration directly corresponds to the actual dispensing action of the drive mechanism. In this way, the user or patient receives a direct and intuitive feedback regarding the progress of the electrically-driven dispensing procedure.

According to another preferred aspect, the electrically-implemented dispensing action of the drive mechanism may further be controllable by the magnitude of the force acting on the dose element, e.g. in distal direction. Hence, the drive mechanism may be implemented in such a way, that a distally directed force or pressure above a predefined level has to be permanently present at the dose element during a dose dispensing procedure. As soon as the force drops below said predefined level, the dispensing procedure may be interrupted and stopped.

However, by mechanically decoupling the dose element and the drive mechanism, the dispensing force required to be applied to a dose element can be effectively reduced. Consequently, the threshold of a distally directed force for initiating or conducting a dose dispensing procedure may be lowered compared to manually and all-mechanically operated drug delivery devices. Interaction of position, rotation and force sensors with the electrically implemented drive mechanism may provide a kind of servo-mechanism that allows to amplify mechanical forces present at the dose element. Even though comparatively large dispensing forces may be originally required with a particular type of cartridge, the actuation forces to be provided by the end user with the present device may be kept on a comparatively low level.

According to a further embodiment, the drug delivery device is readily equipped with a cartridge at least partially filled with the medicament. The cartridge is preferably arranged in a distal portion of the housing of the drug delivery device, which serves as a cartridge holder. The drug delivery device may be designed as disposable or reusable device. When designed as disposable device, the entire drug delivery device is to be discarded when the content of the cartridge is used up. Otherwise, when designed as reusable device, an empty cartridge may be replaced by a filled one.

Furthermore, and according to another aspect, the invention also relates to a method of operating a drive mechanism of a drug delivery device. Said method starts with a dose element being positioned in a specific configuration relative to a housing of the drug delivery device. Even though the dose element is mechanically decoupled from the drive mechanism, it mimics and/or provides a control means to set and/or to dispense a predefined dose of the medicament. In a first step, the position and/or orientation of the dose element relative to the housing is detected and based on said position or orientation, the size of the dose to be dispensed is determined.

Depending on the determined or calculated size of the dose, an electrically driven or automated dose dispensing procedure is conducted and/or controlled. Said dispensing may be triggered by depressing the dose element. During dose dispensing, the dose element is displaced and/or rotated towards its initial position and/or towards its initial orientation and reaches the same upon termination of a dose dispensing action. Movement and/or rotation of the dose element is controlled by the electrically implemented drive or control mechanism of the drug delivery device.

Furthermore, depending on the type of mechanical device to be imitated the position or orientation of the dose element after completion of the dose dispensing action may also vary from an initial position or configuration, the dose element comprises prior to a dose setting action.

In this context it is further to be noted, that the method is particularly adapted to the use of the drug delivery device. Hence, all features and embodiments described and claimed in view of the drug delivery device also refer to said method accordingly.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His -Gly-Glu-Gly-Thr-Phe-Thr-Ser-Asp-Leu-Ser-Lys-Gln-Met-Glu-Glu-Glu-Ala-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, a preferred embodiment of the invention will be described by making reference to the drawings, in which.

DETAILED DESCRIPTION

Figure 1:
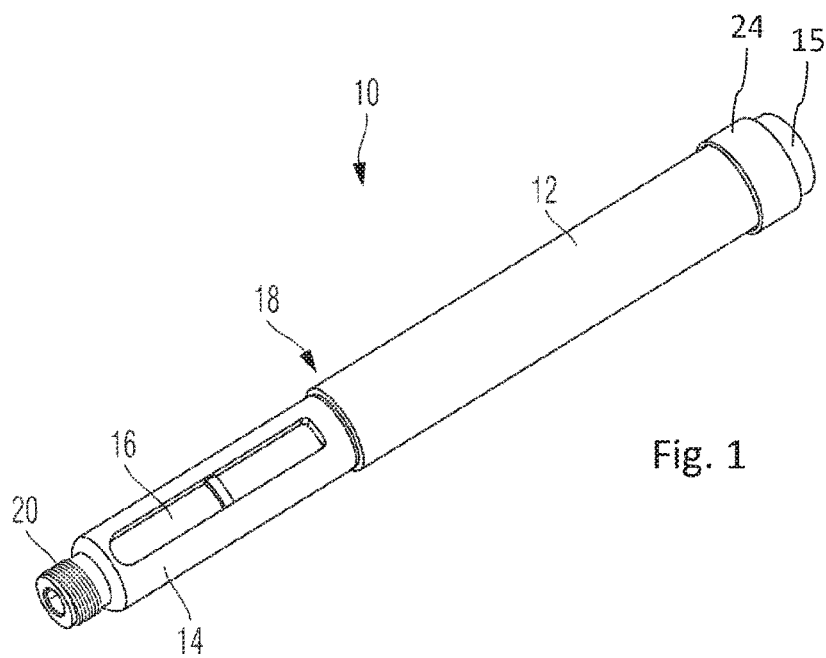
FIG. 1 illustrates a perspective view of a drug delivery device in an initial configuration.
Figure 2:
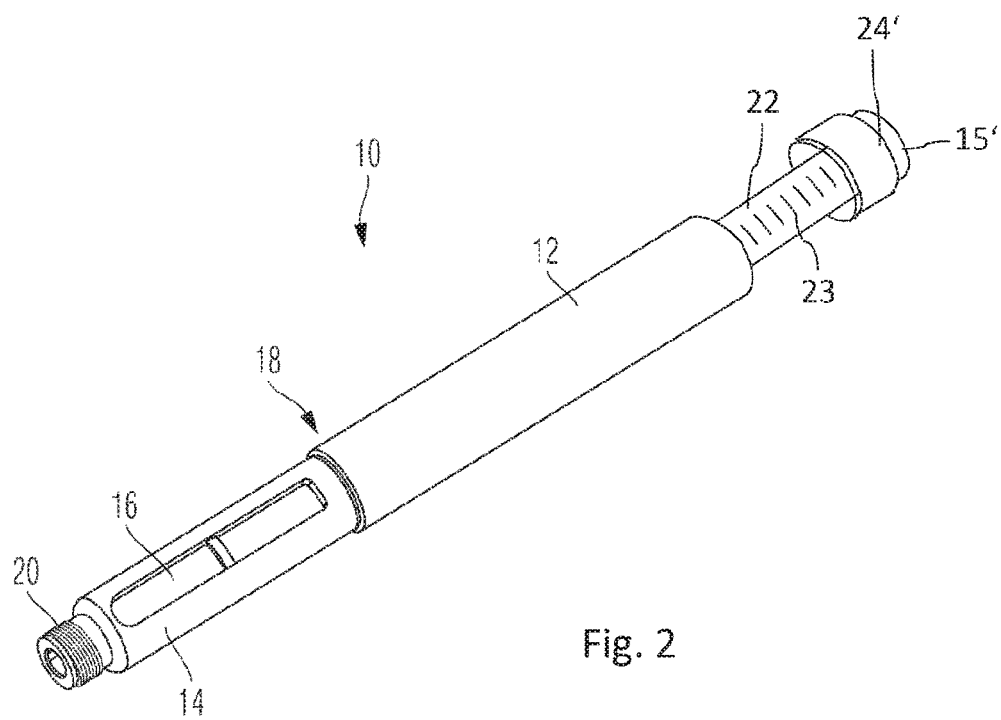
FIG. 2 shows the device according to FIG. 1 with the dose element in a pulled-out configuration.

FIGS. 1 and 2 illustrate a drug delivery device 10 designed as a pen-type injector. The rather elongated and tubular-shaped housing 18 comprises two housing components, namely a proximal body 12 and a distally located cartridge holder 14. Body 12 and cartridge holder 14 are mutually interconnected.

Figure 3:
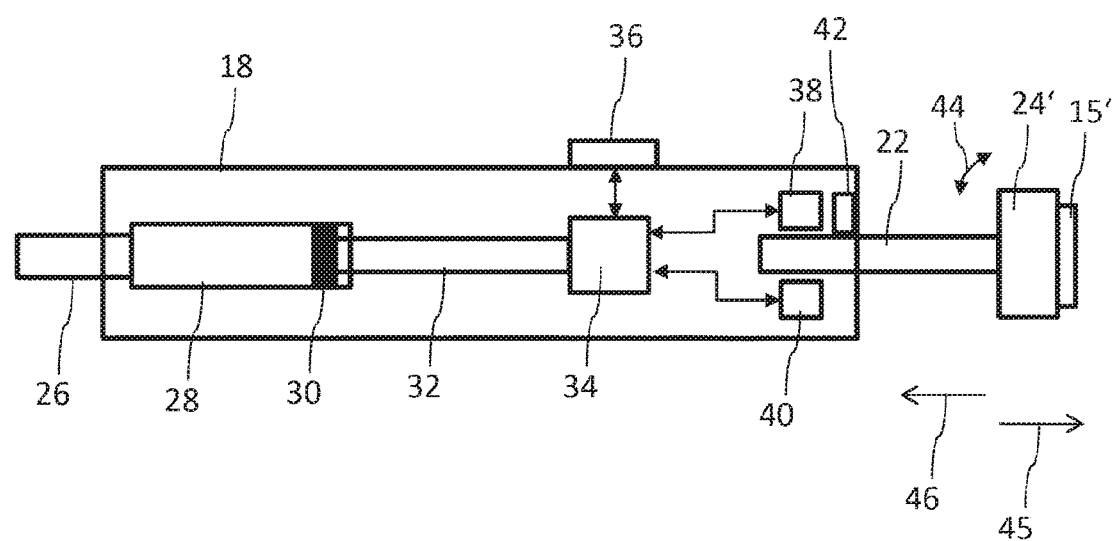
FIG. 3 shows a block diagram of the mutually interacting components of the drug delivery device.

The cartridge holder 14 comprises an inspection window 16 and serves to accommodate a tubular-shaped cartridge 28 typically having a vitreous body and being filled with a liquid medicament. The cartridge 28 as indicated in FIG. 3 typically has a bottle necked distal portion sealed with a pierceable septum. The distal outlet of the cartridge 28 is typically positioned near the distal end face of a threaded socket 20 of the cartridge holder 14. This socket 20 provides a mount for a needle hub 26 having an injection needle and being adapted to be screwed onto said socket 20.

The double-tipped needle assembly 26, as for instance indicated in FIG. 3 penetrates the distal septum of the cartridge 28 and allows to dispense and to inject the liquid medicament into biological tissue.

The proximal housing component 12 is adapted to receive and to accommodate a drive mechanism, which is illustrated in FIG. 3 in a rather simplified way. The drive mechanism comprises at least a piston rod 32 to become operably engaged with a proximally located piston 30 of the cartridge 28. Displacing the piston 30 in distal direction, hence to the left in FIG. 3, leads to a dispensing of the medicament provided in the cartridge 28.

Such distally directed motion of the piston 30 is to be induced by the correspondingly displaceable piston rod 32, which is driven by an electro-mechanical drive 34. The present device 10 comprises an electro-mechanically implemented drive mechanism 32, 34, wherein electrical power is transformed to a distally directed motion of the piston rod 32. The drive 34 and/or a respective control element not explicitly shown here, are preferably coupled with a display element 36 providing dispensing related information to a user or to medical staff.

The drug delivery device 10 further comprises a dose element 15, 24, by way of which the size of a dose to be dispensed can be set and/or modified on request. The dose element 15, 24 comprises for instance a dose button 15 to be depressed in distal direction 46 in order to start a dose dispensing procedure. Furthermore, the dose element comprises a dose dial 24, by way of which the entire dose element 15, 24 can be transferred from an initial configuration as shown in FIG. 1 to a pulled-out configuration 15', 24', as shown in FIG. 2. The dose element 15, 24 may be pulled-out either by way of a longitudinally directed slide movement in proximal direction 45 or by way of a screw motion 44.

In another but not illustrated embodiment, the dose element is rotationally supported on the housing. In this way, the dose setting and/or dose dispensing is controlled by exclusively rotating the dose dial relative to the housing. The dose element does not move in axial direction and is not subject to a screw motion.

Moreover, in a further and not illustrated alternative, the dose element may only comprise a rotatable knob, resembling the dose element 24 but does not comprise a dose element 15 at its proximal free end. Then, the dose element may be screwed and/or pulled out from the body 12 for the purpose of dose setting. A dose dispensing action may be triggered in a different way, e.g. by pressing another button extending radially outwardly from the body 12 and being not further illustrated here.

The dose dial 24 and the push button 15 are supported on a cylindrical rod 22 featuring a scale 23 on its outer circumference. Hence, by pulling out the dose element 15, 24 the scale 23 provided on the rod 22 becomes visible and may therefore indicate the size of the set dose. In the present configuration it is of particular benefit, that the axial or longitudinal displacement of the dose element 15, 24 relative to the housing 18 and/or relative to the body 12 is directly indicative of the size of said dose. However, the scale 23 may be provided as an optional feature. Generally, there are many different ways on how to visually illustrate the size of the set dosage. The housing 12 may for instance comprise an electronically implemented display element not explicitly illustrated here.

As further indicated in FIG. 3, the dose element 24, 15 is mechanically decoupled from the drive 34 and from the piston rod 32. A longitudinally and proximally directed pull-out motion 45 of the rod 22 is detected and measured by a sensor element 38. Depending on the measured distance, the rod 22 has been pulled-out in distal direction 45, the size of a dose to be injected is set. Hence, a signal generated by the sensor is processed by a control element or by the drive 34 in order to determine the size of the dose.

Depressing the dose button 15' in distal direction and applying a respective distally directed force 46 on said button 15' will be detected by a force sensor 42. Once a force above a predefined threshold is detected, a respective dose-dispensing action will be triggered by the drive 34. Additionally, during a dose dispensing procedure, an actuator element 40 mechanically engaged with the rod 22 may return the rod 22 and the dose element 15, 24 into their initial position as illustrated for instance in FIG. 1. The actuator is designed as a separate actuator and is exclusively adapted to move the rod 22 in distal direction during the electrically implemented dose injection procedure.

In this way, the electro-mechanically implemented drive mechanism 32, 34 replicates and imitates the overall behaviour of a conventional manually operated drug delivery device.

With the present device 10 and its functionality, users being accustomed to manually operated drug delivery devices can more easily get accustomed to electro-mechanically operated drug delivery devices 10. Moreover, the force 46 to be applied to the dose button 15 can be kept at a comparatively low level compared to conventional or manually operated devices. Generally, the force level can be kept at a comparatively low level compared to a manually implemented drug delivery device. In this way, the electro-mechanical drive mechanism 32, 34 may simulate a servo drive.

Also, since the automated injection procedure may be controlled by a force sensor, a dispensing action may even be interrupted, e.g. when the pressure applied to the dose button 15 drops below a predefined threshold during a dispensing action.

The invention claimed is:

1. A drug delivery device for setting and dispensing of a dose of a medicament comprising:

a housing configured to accommodate a cartridge filled with the medicament, an electro-mechanically implemented drive mechanism comprising an electrical drive, wherein the drive mechanism is operably engageable with the cartridge and configured to expel a predefined dose of the medicament from the cartridge, wherein the electrical drive is operable to apply a mechanical force to the cartridge, at least one dose element displaceably arranged relative to the housing configured to set or to dispense the dose of the medicament, at least one force sensor to determine a force acting on the dose element during expelling of the predefined dose of the medicament from the cartridge, wherein the dose element and the drive mechanism are permanently mechanically decoupled from each other.

2. The drug delivery device according to claim 1, wherein the dose element is configured to set and to dispense the dose of the medicament.

3. The drug delivery device according to claim 2, wherein the dose element is translationally or rotatably mounted relative to the housing.

4. The drug delivery device according to claim 1, wherein the dose element is translationally and rotatably mounted relative to the housing.

5. The drug delivery device according to claim 1, wherein a position or orientation of the dose element relative to the housing is indicative of a size of the dose to be injected by the device.

6. The drug delivery device according to claim 5, wherein the dose element comprises a scale, which according to the position or orientation of the dose element relative to the housing is indicative of a number of units of the medicament to be injected by the device.

7. The drug delivery device according to claim 1, wherein the dose element is operable to initiate or to control a dose dispensing operation of the drive mechanism.

8. The drug delivery device according to claim 1, further comprising at least one of a position sensor and a rotation sensor to detect the position or orientation of the dose element relative to the housing.

9. The drug delivery device according to claim 8, wherein at least one of the position sensor and rotation sensor is implemented optically, magnetically, or electrically.

10. The drug delivery device according to claim 1, further comprising an actuator to displace or to rotate the dose element into an initial position or initial orientation during an electrically operated dose dispensing action of the drive mechanism.

11. The drug delivery device according to claim 10, wherein the displacement or rotation of the dose element directly corresponds to the electrically operated dose dispensing action of the drive mechanism.

12. The drug delivery device according to claim 10, wherein the actuator is controlled by the electrically implemented drive mechanism such that a momentary position or movement of the dose element reflects the actual dose dispensing procedure conducted by the drive mechanism.

13. The drug delivery device according to claim 1, wherein a dispensing action of the drive mechanism is controllable by a magnitude of the force acting on the dose element.

14. The drug delivery device according to claim 13, wherein a velocity of an electro-mechanically implemented dose dispensing is governed by the magnitude of the force applied acting on the dose element.

15. The drug delivery device according to claim 1, wherein a distally directed force above a predefined level is required during dose dispensing and wherein dose dispensing is interrupted as soon as the distally directed force drops below a threshold.

16. The drug delivery device according to claim 1, wherein the cartridge is at least partially filled with the medicament and wherein the cartridge is arranged in the housing.

17. The drug delivery device according to claim 16, wherein the drive mechanism comprises a piston rod to exert distally directed pressure to a piston of the cartridge to expel a dose of the medicament from the cartridge.

18. The drug delivery device according to claim 17, wherein the drive mechanism is configured to transform electrical power into a distally directed motion of the piston rod.

19. The drug delivery device according to claim 1, wherein the dose element comprises a dose button depressible in a distal direction to start a dose dispensing procedure.

20. The drug delivery device according to claim 1, wherein the dose element comprises a dose dial to transfer the entire dose element from an initial configuration to a proximally pulled-out configuration.

21. A method for operating a drive mechanism of a drug delivery device, wherein the drive mechanism comprises an electrical drive, the method comprising:

moving a dose element relative to a housing of the drug delivery device for setting of a dose, the dose element being at least one of translationally and rotationally movable relative to the housing, detecting a position or orientation of the dose element relative to the housing of the drug delivery device, determining a size of the dose to be dispensed on a basis of the relative position or orientation of the dose element relative to the housing, controlling an electrically driven dose dispensing procedure, by controlling operation of the electrical drive on a basis of the size of the dose, wherein the electrical drive is operable to generate and to apply a mechanical force to a cartridge filled with a medicament when the cartridge is arranged inside the housing, and controlling displacement of the dose element towards an initial position or initial orientation during the dose dispensing procedure.

22. The method of claim 21, wherein the method comprises detecting the position and orientation of the dose element relative to the housing of the drug delivery device.

23. The method of claim 21, wherein the method comprises determining a size of the dose to be dispensed on the basis of the relative position and orientation.

24. The method of claim 21, wherein the method comprises controlling displacement of displacing the dose element in an initial position and orientation during the dose dispensing procedure.

* * * * *